United States Patent
Shelton, IV

(10) Patent No.: US 8,020,743 B2
(45) Date of Patent: Sep. 20, 2011

(54) POWERED ARTICULATABLE SURGICAL CUTTING AND FASTENING INSTRUMENT WITH FLEXIBLE DRIVE MEMBER

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 178 days.

(21) Appl. No.: 12/251,816

(22) Filed: Oct. 15, 2008

(65) Prior Publication Data

US 2010/0089974 A1 Apr. 15, 2010

(51) Int. Cl.
*A61B 17/072* (2006.01)

(52) U.S. Cl. ............... 227/180.1; 227/175.1; 227/19

(58) Field of Classification Search .... 227/175.1–182.1, 227/19; 606/219
See application file for complete search history.

(56) References Cited

U.S. PATENT DOCUMENTS

| | | |
|---|---|---|
| 2,853,074 A | 9/1958 | Olson |
| 3,490,675 A | 1/1970 | Green et al. |
| 3,551,987 A | 1/1971 | Wilkinson |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,619,262 A | 10/1986 | Taylor |

(Continued)

FOREIGN PATENT DOCUMENTS

CA 2458946 A1 3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Lindsay Low

(57) ABSTRACT

A surgical cutting and fastening instrument is disclosed. According to various embodiments, the instrument may include a handle assembly that has an elongate shaft attached thereto. An end effector that is configured to support a staple cartridge may be pivotally coupled to the elongate shaft. The handle assembly may support a generator of rotary motion that interfaces with a rotary drive system that may include a flexible drive shaft. The flexible drive shaft may be configured to impart a driving motion to a knife supporting assembly supported within the end effector. Such arrangement enables the end effector to be fired while being articulated relative to the elongate shaft.

20 Claims, 11 Drawing Sheets

U.S. PATENT DOCUMENTS

| | | | |
|---|---|---|---|
| 4,629,107 A | 12/1986 | Fedotov et al. | |
| 4,655,222 A | 4/1987 | Florez et al. | |
| 4,664,305 A | 5/1987 | Blake, III et al. | |
| 4,671,445 A | 6/1987 | Barker et al. | |
| 4,715,520 A | 12/1987 | Roehr, Jr. et al. | |
| 4,728,020 A | 3/1988 | Green et al. | |
| 4,752,024 A | 6/1988 | Green et al. | |
| 4,754,909 A | 7/1988 | Barker et al. | |
| 4,767,044 A | 8/1988 | Green | |
| 4,805,823 A | 2/1989 | Rothfuss | |
| 4,809,695 A | 3/1989 | Gwathmey et al. | |
| 4,817,847 A | 4/1989 | Redtenbacher et al. | |
| 4,819,853 A | 4/1989 | Green | |
| 4,821,939 A | 4/1989 | Green | |
| 4,869,414 A | 9/1989 | Green et al. | |
| 4,869,415 A | 9/1989 | Fox | |
| 4,941,623 A | 7/1990 | Pruitt | |
| 4,944,443 A | 7/1990 | Oddsen et al. | |
| 5,065,929 A | 11/1991 | Schulze et al. | |
| 5,071,430 A | 12/1991 | de Salis et al. | |
| 5,129,570 A | 7/1992 | Schulze et al. | |
| 5,137,198 A | 8/1992 | Nobis et al. | |
| 5,139,513 A | 8/1992 | Segato | |
| 5,158,567 A | 10/1992 | Green | |
| 5,221,036 A | 6/1993 | Takase | |
| 5,222,975 A | 6/1993 | Crainich | |
| 5,258,009 A | 11/1993 | Conners | |
| 5,282,829 A | 2/1994 | Hermes | |
| 5,304,204 A | 4/1994 | Bregen | |
| 5,342,395 A | 8/1994 | Jarrett et al. | |
| 5,342,396 A | 8/1994 | Cook | |
| 5,350,400 A | 9/1994 | Esposito et al. | |
| 5,366,479 A | 11/1994 | McGarry et al. | |
| 5,383,880 A * | 1/1995 | Hooven | 606/142 |
| 5,413,272 A | 5/1995 | Green et al. | |
| 5,417,361 A | 5/1995 | Williamson, IV | |
| 5,425,745 A | 6/1995 | Green et al. | |
| 5,465,895 A | 11/1995 | Knodel et al. | |
| 5,478,354 A | 12/1995 | Tovey et al. | |
| 5,480,089 A | 1/1996 | Blewett | |
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,509,596 A | 4/1996 | Green et al. | |
| 5,529,235 A | 6/1996 | Boiarski et al. | |
| 5,535,934 A | 7/1996 | Boiarski et al. | |
| 5,540,375 A | 7/1996 | Bolanos et al. | |
| 5,542,594 A | 8/1996 | McKean et al. | |
| 5,553,765 A | 9/1996 | Knodel et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,241 A | 10/1996 | Knodel et al. | |
| 5,564,615 A | 10/1996 | Bishop et al. | |
| 5,577,654 A | 11/1996 | Bishop | |
| 5,580,067 A | 12/1996 | Hamblin et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,601,224 A | 2/1997 | Bishop et al. | |
| 5,603,443 A | 2/1997 | Clark et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,609,285 A | 3/1997 | Grant et al. | |
| 5,628,446 A * | 5/1997 | Geiste et al. | 227/175.1 |
| 5,630,539 A | 5/1997 | Plyley et al. | |
| 5,630,540 A | 5/1997 | Blewett | |
| 5,632,432 A | 5/1997 | Schulze et al. | |
| 5,632,433 A | 5/1997 | Grant et al. | |
| 5,634,584 A | 6/1997 | Okorocha et al. | |
| 5,636,780 A | 6/1997 | Green et al. | |
| 5,639,008 A | 6/1997 | Gallagher et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,667,527 A | 9/1997 | Cook | |
| 5,669,544 A | 9/1997 | Schulze et al. | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,685,474 A | 11/1997 | Seeber | |
| 5,690,269 A | 11/1997 | Bolanos et al. | |
| 5,692,668 A | 12/1997 | Schulze et al. | |
| 5,697,543 A | 12/1997 | Burdorff | |
| 5,704,534 A | 1/1998 | Huitema et al. | |
| 5,711,472 A | 1/1998 | Bryan | |
| 5,713,505 A | 2/1998 | Huitema | |
| 5,715,987 A | 2/1998 | Kelley et al. | |
| 5,718,360 A | 2/1998 | Green et al. | |
| 5,725,554 A | 3/1998 | Simon et al. | |
| 5,732,871 A | 3/1998 | Clark et al. | |
| 5,732,872 A | 3/1998 | Bolduc et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,256 A | 6/1998 | Mastri et al. | |
| 5,779,130 A * | 7/1998 | Alesi et al. | 227/176.1 |
| 5,779,131 A | 7/1998 | Knodel et al. | |
| 5,779,132 A | 7/1998 | Knodel et al. | |
| 5,782,397 A * | 7/1998 | Koukline | 227/176.1 |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,799,857 A | 9/1998 | Robertson et al. | |
| 5,820,009 A | 10/1998 | Melling et al. | |
| 5,826,776 A | 10/1998 | Schulze et al. | |
| 5,829,662 A | 11/1998 | Allen et al. | |
| 5,836,503 A | 11/1998 | Ehrenfels et al. | |
| 5,839,639 A | 11/1998 | Sauer et al. | |
| 5,855,311 A | 1/1999 | Hamblin et al. | |
| 5,865,361 A | 2/1999 | Milliman et al. | |
| 5,871,135 A | 2/1999 | Williamson, IV et al. | |
| 5,901,895 A | 5/1999 | Heaton et al. | |
| 5,911,353 A | 6/1999 | Bolanos et al. | |
| 5,915,616 A | 6/1999 | Viola et al. | |
| 5,941,442 A | 8/1999 | Geiste et al. | |
| 5,954,259 A * | 9/1999 | Viola et al. | 227/176.1 |
| 6,010,054 A | 1/2000 | Johnson et al. | |
| 6,032,849 A | 3/2000 | Mastri et al. | |
| 6,083,242 A | 7/2000 | Cook | |
| 6,099,551 A | 8/2000 | Gabbay | |
| 6,102,271 A | 8/2000 | Longo et al. | |
| 6,119,913 A | 9/2000 | Adams et al. | |
| 6,126,058 A | 10/2000 | Adams et al. | |
| 6,171,330 B1 | 1/2001 | Benchetrit | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,330,965 B1 | 12/2001 | Milliman et al. | |
| 6,387,113 B1 | 5/2002 | Hawkins et al. | |
| RE37,814 E | 8/2002 | Allgeyer | |
| 6,443,973 B1 | 9/2002 | Whitman | |
| 6,488,197 B1 | 12/2002 | Whitman | |
| 6,491,201 B1 | 12/2002 | Whitman | |
| 6,505,768 B2 | 1/2003 | Whitman | |
| 6,517,565 B1 | 2/2003 | Whitman et al. | |
| 6,578,751 B2 | 6/2003 | Hartwick | |
| 6,588,643 B2 | 7/2003 | Bolduc et al. | |
| 6,601,749 B2 | 8/2003 | Sullivan et al. | |

| | | |
|---|---|---|
| 6,616,686 B2 | 9/2003 | Coleman et al. |
| 6,619,529 B2 | 9/2003 | Green et al. |
| 6,629,988 B2 | 10/2003 | Weadock |
| 6,644,532 B2 | 11/2003 | Green et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,769,594 B2 | 8/2004 | Orban, III |
| 6,786,382 B1 | 9/2004 | Hoffman |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,108,709 B2 | 9/2006 | Cummins |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 * | 7/2008 | Smith et al. ............... 227/175.1 |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,575,144 B2 * | 8/2009 | Ortiz et al. ............... 227/175.1 |
| 7,631,793 B2 | 12/2009 | Rethy et al. |
| 7,665,646 B2 | 2/2010 | Prommersberger |
| 7,717,312 B2 | 5/2010 | Beetel |
| 7,766,209 B2 | 8/2010 | Baxter, III et al. |
| 7,793,812 B2 | 9/2010 | Moore et al. |
| 7,810,692 B2 | 10/2010 | Hall et al. |
| 2002/0117534 A1 | 8/2002 | Green et al. |
| 2004/0006372 A1 | 1/2004 | Racenet et al. |
| 2004/0094597 A1 * | 5/2004 | Whitman et al. ............ 227/180.1 |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0254608 A1 | 12/2004 | Huitema et al. |
| 2005/0059997 A1 | 3/2005 | Bauman et al. |
| 2005/0103819 A1 | 5/2005 | Racenet et al. |
| 2005/0131457 A1 | 6/2005 | Douglas et al. |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0108393 A1 | 5/2006 | Heinrich et al. |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 * | 2/2007 | Whitman et al. ............ 227/175.1 |
| 2007/0034668 A1 | 2/2007 | Holsten et al. |
| 2007/0045379 A1 | 3/2007 | Shelton, IV |
| 2007/0073341 A1 | 3/2007 | Smith |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |

| Publication No. | Date | Inventor(s) |
|---|---|---|
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175947 A1* | 8/2007 | Ortiz et al. .............. 227/175.1 |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308606 A1 | 12/2008 | Timm et al. |
| 2008/0308607 A1 | 12/2008 | Timm et al. |
| 2008/0308608 A1 | 12/2008 | Prommersberger |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314960 A1 | 12/2008 | Marczyk et al. |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0096435 A1 | 4/2010 | Fuchs et al. |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |

| | | | | | | |
|---|---|---|---|---|---|---|
| DE | 9412228 U | 9/1994 | | EP | 1702567 A2 | 9/2006 |
| DE | 19924311 A1 | 11/2000 | | EP | 1129665 B1 | 11/2006 |
| DE | 69328576 T2 | 1/2001 | | EP | 1256317 B1 | 12/2006 |
| DE | 20112837 U1 | 10/2001 | | EP | 1728473 A1 | 12/2006 |
| DE | 20121753 U1 | 4/2003 | | EP | 1728475 A2 | 12/2006 |
| DE | 10314072 A1 | 10/2004 | | EP | 1479346 B1 | 1/2007 |
| EP | 0122046 A1 | 10/1984 | | EP | 1484024 B1 | 1/2007 |
| EP | 0070230 B1 | 10/1985 | | EP | 1754445 A2 | 2/2007 |
| EP | 0033548 B1 | 5/1986 | | EP | 1759812 A1 | 3/2007 |
| EP | 0276104 A2 | 7/1988 | | EP | 1769756 A1 | 4/2007 |
| EP | 0639349 A2 | 2/1994 | | EP | 1769758 A1 | 4/2007 |
| EP | 0324636 B1 | 3/1994 | | EP | 1785097 A2 | 5/2007 |
| EP | 0593920 A1 | 4/1994 | | EP | 1790293 A2 | 5/2007 |
| EP | 0600182 A2 | 6/1994 | | EP | 1800610 A1 | 6/2007 |
| EP | 0630612 A1 | 12/1994 | | EP | 1300117 B1 | 8/2007 |
| EP | 0634144 A1 | 1/1995 | | EP | 1813199 A1 | 8/2007 |
| EP | 0646356 A2 | 4/1995 | | EP | 1813201 A1 | 8/2007 |
| EP | 0646357 A1 | 4/1995 | | EP | 1813203 A2 | 8/2007 |
| EP | 0653189 A2 | 5/1995 | | EP | 1813207 A1 | 8/2007 |
| EP | 0669104 A1 | 8/1995 | | EP | 1813209 A1 | 8/2007 |
| EP | 0511470 B1 | 10/1995 | | EP | 1402821 B1 | 12/2007 |
| EP | 0679367 A2 | 11/1995 | | EP | 1872727 A1 | 1/2008 |
| EP | 0392547 B1 | 12/1995 | | EP | 1839596 A2 | 2/2008 |
| EP | 0685204 A1 | 12/1995 | | EP | 1897502 A1 | 3/2008 |
| EP | 0699418 A1 | 3/1996 | | EP | 1702568 B1 | 7/2008 |
| EP | 0702937 A1 | 3/1996 | | EP | 1970014 A1 | 9/2008 |
| EP | 0705571 A1 | 4/1996 | | EP | 1980213 A2 | 10/2008 |
| EP | 0484677 B2 | 6/1996 | | EP | 1759645 B1 | 11/2008 |
| EP | 0541987 B1 | 7/1996 | | EP | 1693008 B1 | 12/2008 |
| EP | 0667119 B1 | 7/1996 | | EP | 2000102 A2 | 12/2008 |
| EP | 0770355 A1 | 5/1997 | | EP | 1749486 B1 | 3/2009 |
| EP | 0503662 B1 | 6/1997 | | EP | 2090256 A2 | 8/2009 |
| EP | 0578425 B1 | 9/1997 | | EP | 1813206 B1 | 4/2010 |
| EP | 0625335 B1 | 11/1997 | | FR | 999646 A | 2/1952 |
| EP | 0552423 B1 | 1/1998 | | FR | 1112936 A | 3/1956 |
| EP | 0592244 B1 | 1/1998 | | FR | 2765794 A | 1/1999 |
| EP | 0648476 B1 | 1/1998 | | GB | 939929 A | 10/1963 |
| EP | 0676173 B1 | 9/1998 | | GB | 1210522 A | 10/1970 |
| EP | 0603472 B1 | 11/1998 | | GB | 2336214 A | 10/1999 |
| EP | 0605351 B1 | 11/1998 | | JP | 6007357 A | 1/1994 |
| EP | 0878169 A1 | 11/1998 | | JP | 7051273 A | 2/1995 |
| EP | 0879742 A1 | 11/1998 | | JP | 8033641 A | 2/1996 |
| EP | 0760230 B1 | 2/1999 | | JP | 8229050 A | 9/1996 |
| EP | 0537572 B1 | 6/1999 | | JP | 2000287987 A | 10/2000 |
| EP | 0552050 B1 | 5/2000 | | JP | 2001286477 A | 10/2001 |
| EP | 1090592 A1 | 4/2001 | | JP | 2002369820 A | 12/2002 |
| EP | 1256318 B1 | 5/2001 | | JP | 2005505322 T | 2/2005 |
| EP | 0908152 B1 | 1/2002 | | JP | 2005103293 A | 4/2005 |
| EP | 0872213 B1 | 5/2002 | | RU | 2187249 C2 | 8/2002 |
| EP | 1238634 A2 | 9/2002 | | RU | 2225170 C2 | 3/2004 |
| EP | 0656188 B1 | 1/2003 | | SU | 1377053 A1 | 2/1988 |
| EP | 0829235 B1 | 6/2003 | | SU | 1561964 A1 | 5/1990 |
| EP | 0813843 B1 | 10/2003 | | SU | 1722476 A1 | 3/1992 |
| EP | 0741996 B1 | 2/2004 | | WO | WO 93/08755 A1 | 5/1993 |
| EP | 0705570 B1 | 4/2004 | | WO | WO 95/18572 A1 | 7/1995 |
| EP | 1086713 B1 | 5/2004 | | WO | WO 95/23557 A1 | 9/1995 |
| EP | 1426012 A1 | 6/2004 | | WO | WO 95/29639 A1 | 11/1995 |
| EP | 0888749 B1 | 9/2004 | | WO | WO 96/22055 A1 | 7/1996 |
| EP | 1477119 A1 | 11/2004 | | WO | WO 96/35464 A1 | 11/1996 |
| EP | 1479345 A1 | 11/2004 | | WO | WO 97/34533 A1 | 9/1997 |
| EP | 1479347 A1 | 11/2004 | | WO | WO 97/39688 A2 | 10/1997 |
| EP | 1479348 A1 | 11/2004 | | WO | WO 98/17180 A1 | 4/1998 |
| EP | 1520521 A1 | 4/2005 | | WO | WO 98/30153 A1 | 7/1998 |
| EP | 1520523 A1 | 4/2005 | | WO | WO 99/12483 A1 | 3/1999 |
| EP | 1520525 A1 | 4/2005 | | WO | WO 99/15086 A1 | 4/1999 |
| EP | 1522264 A1 | 4/2005 | | WO | WO 99/34744 A1 | 7/1999 |
| EP | 1550408 A1 | 7/2005 | | WO | WO 99/45849 A1 | 9/1999 |
| EP | 1557129 A1 | 7/2005 | | WO | WO 00/24322 A1 | 5/2000 |
| EP | 1064883 B1 | 8/2005 | | WO | WO 00/57796 A1 | 10/2000 |
| EP | 1157666 B1 | 9/2005 | | WO | WO 00/64365 A1 | 11/2000 |
| EP | 1621138 A2 | 2/2006 | | WO | WO 00/72762 A1 | 12/2000 |
| EP | 1621139 A2 | 2/2006 | | WO | WO 00/72765 A1 | 12/2000 |
| EP | 1621141 A2 | 2/2006 | | WO | WO 01/05702 A1 | 1/2001 |
| EP | 1621145 A2 | 2/2006 | | WO | WO 01/10482 A1 | 2/2001 |
| EP | 1621151 A2 | 2/2006 | | WO | WO 01/54594 A1 | 8/2001 |
| EP | 1652481 A2 | 5/2006 | | WO | WO 01/62158 A2 | 8/2001 |
| EP | 1382303 B1 | 6/2006 | | WO | WO 01/62162 A1 | 8/2001 |
| EP | 1045672 B1 | 8/2006 | | WO | WO 01/62164 A2 | 8/2001 |
| EP | 1617768 B1 | 8/2006 | | WO | WO 01/91646 A1 | 12/2001 |

| | | |
|---|---|---|
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

* cited by examiner

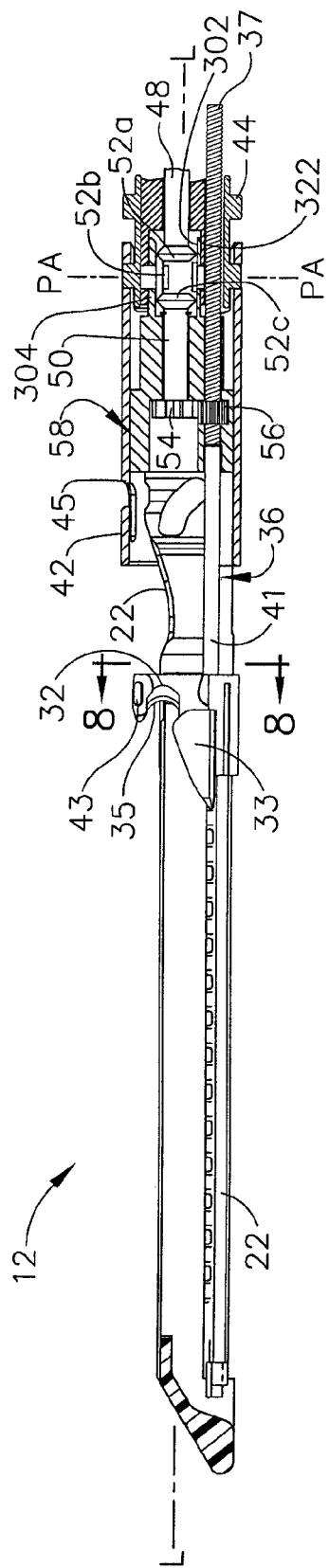
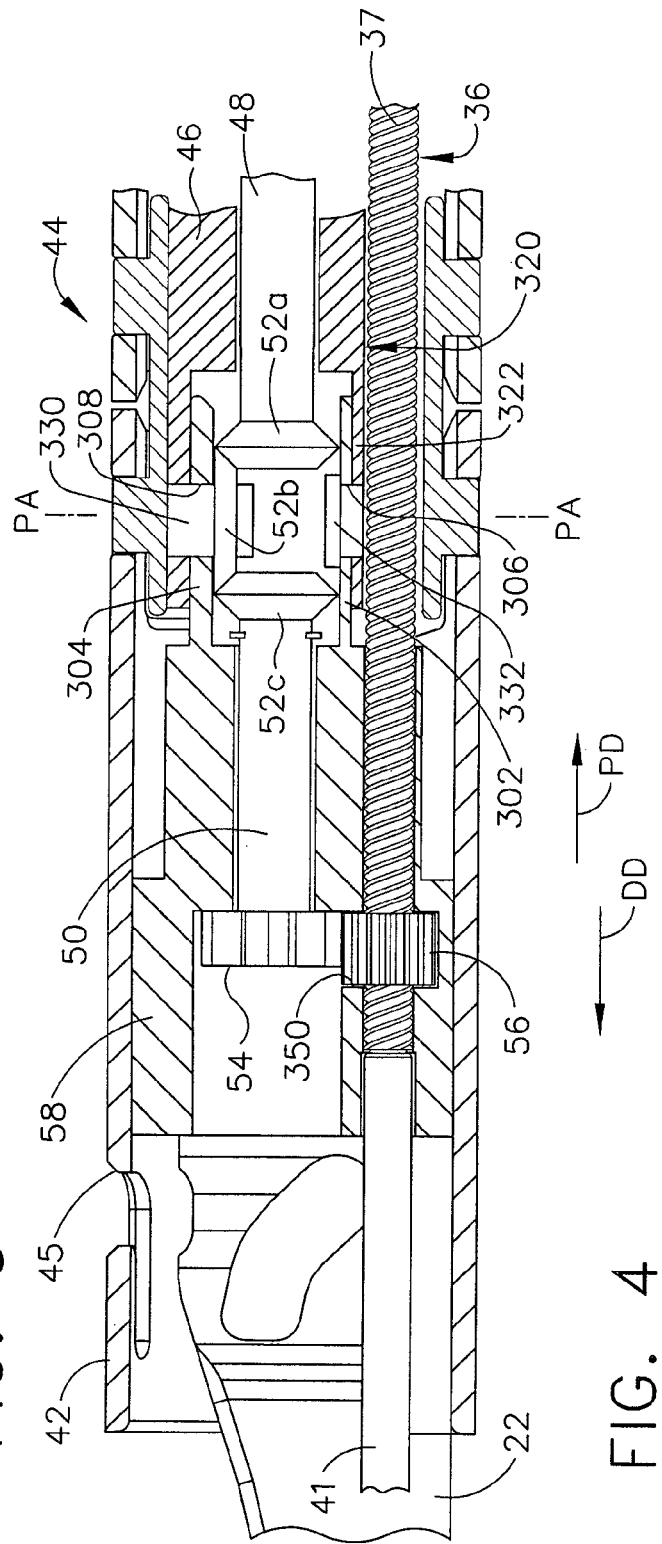
FIG. 3
FIG. 4

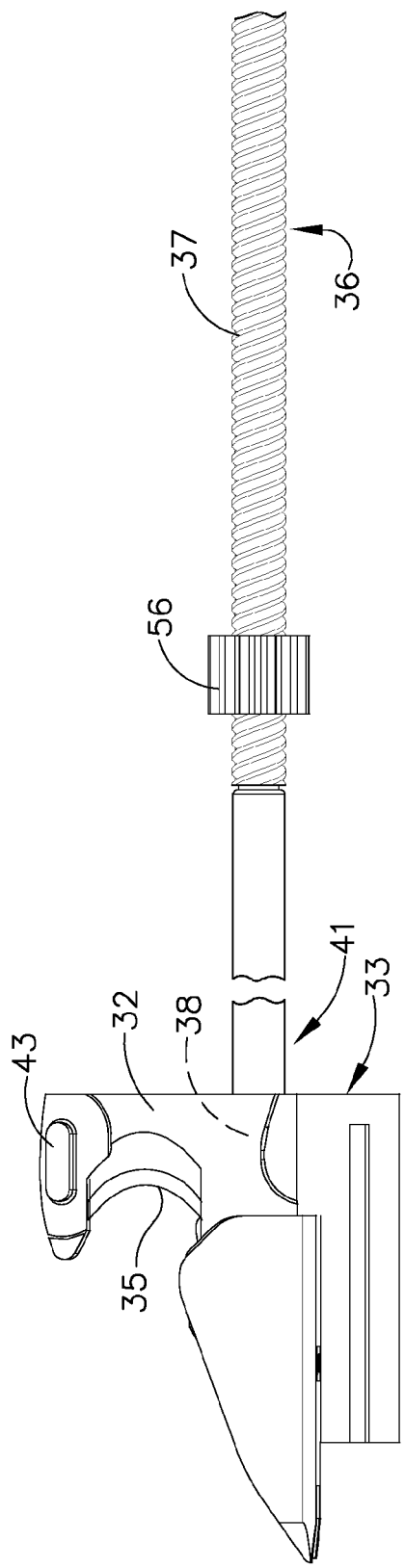
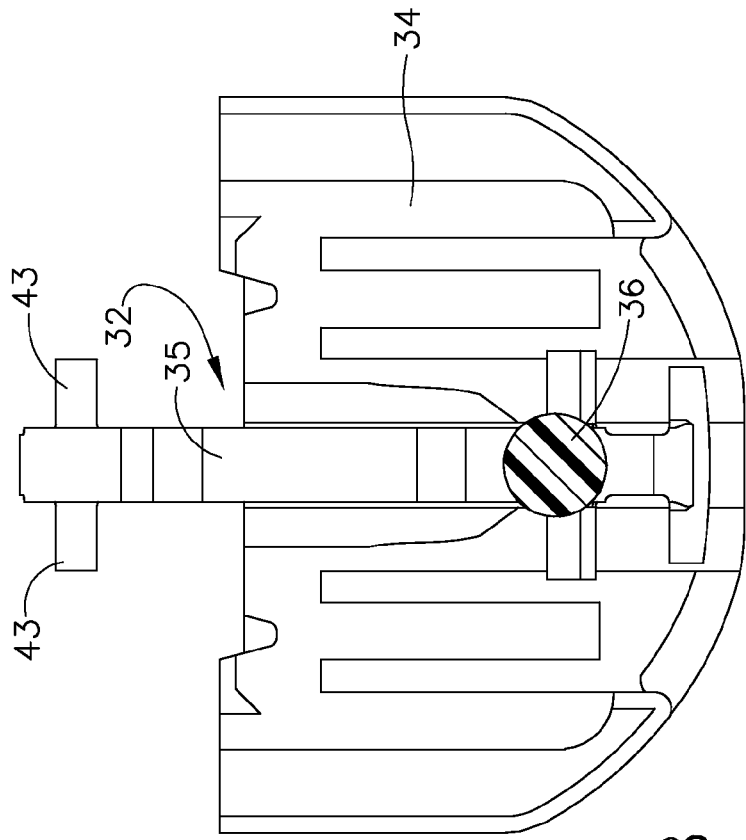
FIG. 7
FIG. 8

POWERED ARTICULATABLE SURGICAL CUTTING AND FASTENING INSTRUMENT WITH FLEXIBLE DRIVE MEMBER

FIELD OF THE INVENTION

The present invention generally concerns surgical cutting and fastening instruments and, more particularly, articulatable motor-driven surgical cutting and fastening instruments.

BACKGROUND

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with a single firing stroke, or multiple firing strokes, depending on the device. Firing the surgical stapler causes severing and stapling the tissue. The simultaneous severing and stapling avoids complications that may arise when performing such actions sequentially with different surgical tools that respectively only sever and staple.

Another surgical stapler is disclosed in U.S. Patent Application Publication No. US 2007/0175959 A1, Ser. No. 11/343,562, filed Aug. 2, 2007, to Shelton, IV et al., the disclosure of which is herein incorporated by reference in its entirety. Various stapler embodiments disclosed in that reference are motor driven. The knife driving member is threaded onto a drive shaft that is supported within the elongate staple channel. The drive shaft does not move axially, but is rotatable within the elongate channel. As the drive shaft is rotated in a first direction, the knife driving member is drawn in a distal direction and as the drive shaft is rotated in an opposite direction, the knife driving member is drawn in a proximal direction.

SUMMARY

In one general aspect, the present invention is directed to a surgical cutting and fastening instrument. According to various embodiments, the instrument may include a handle assembly that supports a generator of rotary motion. An elongate shaft assembly may be operably coupled to the handle assembly such that it defines an elongate axis. An elongate channel may be coupled to the elongate shaft for selective pivotal travel about a pivot axis that is substantially transverse to the elongate axis. The elongate channel may be sized to operably support a staple cartridge therein. The instrument may further include a rotary drive system that comprises a main drive shaft assembly that operably interfaces with the generator of rotary motion. A gear train may be in meshing engagement with the main drive shaft for receiving the rotary motion therefrom. A flexible drive shaft may be in meshing engagement with the gear drive train and be oriented to impart a pushing motion to a knife supporting assembly in the elongate channel to drive the knife supporting assembly in a distal direction upon receipt of a rotary motion in a first direction from the gear drive train.

Other aspects of the present invention are directed to surgical cutting and fastening instrument that may include a handle assembly that supports a generator of rotary motion. An elongate shaft assembly may be operably coupled to the handle assembly. The elongate shaft assembly may define an elongate axis. An elongate channel may be coupled to the elongate shaft for selective pivotal travel about a pivot axis that is substantially transverse to the elongate axis. The elongate channel may be sized to removably support a disposable staple cartridge therein that has a knife supporting assembly therein. The instrument may further include a rotary drive system that comprises a main drive shaft assembly that operably interfaces with the generator of rotary motion. A gear train may be in meshing engagement with the main drive shaft for receiving the rotary motion therefrom. A flexible drive shaft may be movably supported in the elongate shaft and be oriented in meshing engagement with the gear drive train. The flexible dive shaft may also be oriented to extend axially into the disposable staple cartridge to impart an axial pushing motion to the knife supporting assembly to drive the knife supporting assembly in a distal direction within the disposable staple cartridge upon receipt of a rotary motion in a first direction from the gear drive train. The flexible drive shaft may also return into the elongate shaft upon receipt of a rotary motion in a second direction from the gear drive train.

In accordance with another general aspect of the present invention there is provided a surgical cutting and fastening instrument that may include a handle assembly that supports a generator of rotary motion. An elongate shaft assembly may be operably coupled to the handle assembly and define an elongate axis. An elongate channel may be coupled to the elongate shaft for selective pivotal travel about a pivot axis that is substantially transverse to the elongate axis. The elongate channel may be sized to removably support a staple cartridge therein. A reusable knife supporting assembly may be operably supported within the elongate channel for selective axial travel therein between starting and ending positions. The instrument may further include a rotary drive system that comprises a main drive shaft assembly that operably interfaces with the generator of rotary motion. A gear train may be in meshing engagement with the main drive shaft for receiving the rotary motion therefrom. A flexible drive shaft may be coupled to the reusable knife supporting assembly and be movably supported in the elongate shaft. The flexible drive shaft may be in meshing engagement with the gear drive train and be oriented to extend axially into the staple cartridge to drive the knife supporting assembly from the starting position to the ending position upon receipt of a rotary motion in a first direction from the gear drive train and to return the knife supporting assembly to the starting position upon receipt of a rotary motion in a second direction from the gear drive train.

DRAWINGS

Various embodiments of the present invention are described herein by way of example in conjunction with the following figures, wherein FIG. 1 is a perspective view of a surgical cutting and fastening instrument according to various embodiments of the present invention;

FIG. 3 is a partial cross-sectional view of an end effector embodiment of the present invention;

FIG. 4 is an enlarged cross-sectional view of a portion of the articulation joint and end effector of various end effector embodiments of the present invention;

FIG. 7 is a side elevational view of knife supporting assembly and sled and drive shaft arrangement of various embodiments of the present invention;

FIG. 8 is a cross-sectional view of a portion of the cartridge of various embodiments of the present invention taken along line 8-8 in FIG. 3;

DETAILED DESCRIPTION

Figure 1:
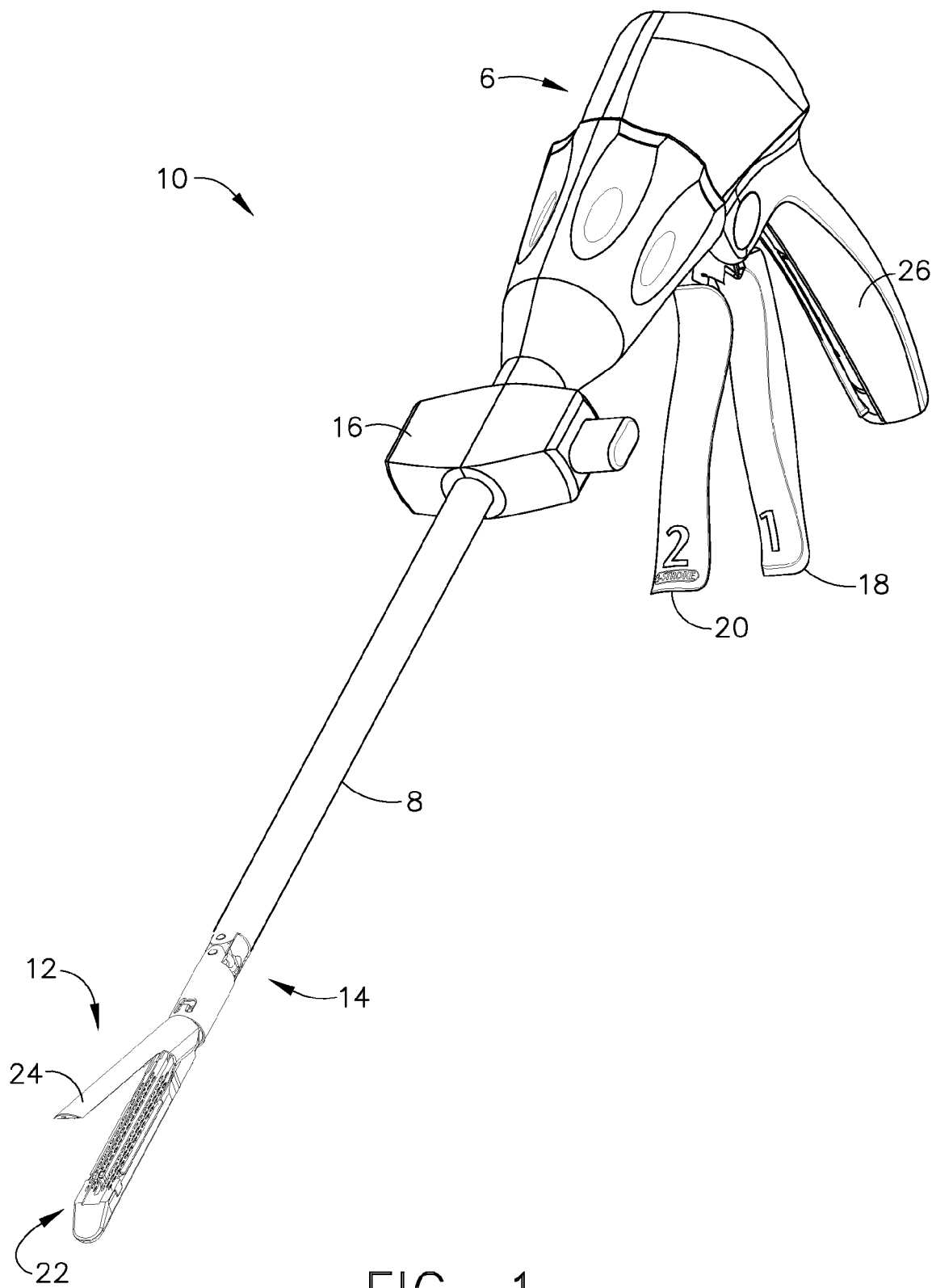
Figure 2:
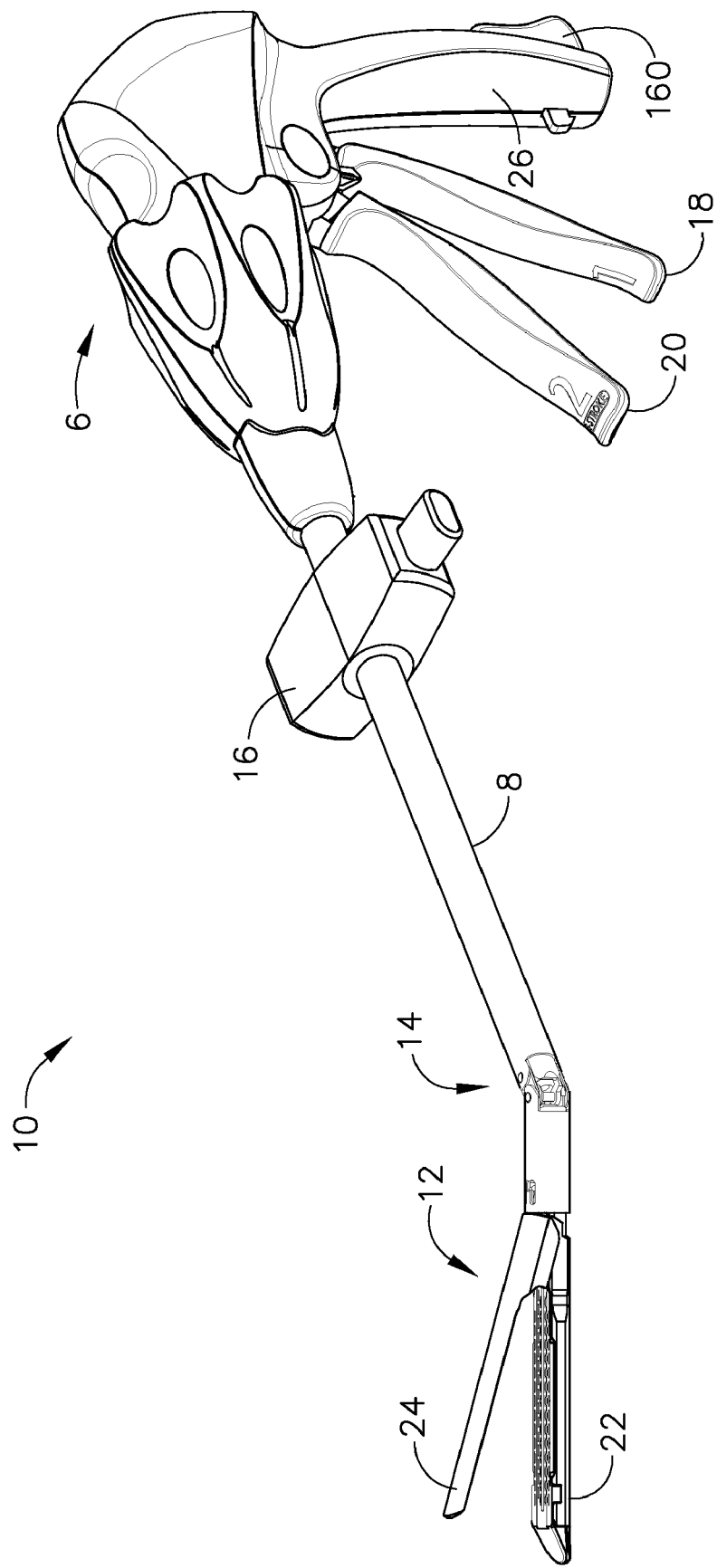
FIG. 2 is another perspective view of the surgical cutting and fastening instrument of FIG. 1 in an articulated position.

FIGS. 1 and 2 depict a surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that according to other embodiments of the present invention, the instrument may be a non-endoscopic surgical cutting and fastening instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8.

In one embodiment, a clinician or operator of the instrument 10 may articulate the end effector 12 relative to the shaft 8 by utilizing the articulation control 16, as described in more detail in pending U.S. Patent Application Publication No. 2007/0158385 A1, filed Jan. 10, 2006, entitled "Surgical Instrument Having An Articulating End Effector," by Geoffrey C. Hueil et al., which is incorporated herein by reference in its entirety.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12.

It will be appreciated that the terms "proximal" and "distal" are used herein with reference to a clinician gripping the handle 6 of the instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18.

Figure 5:
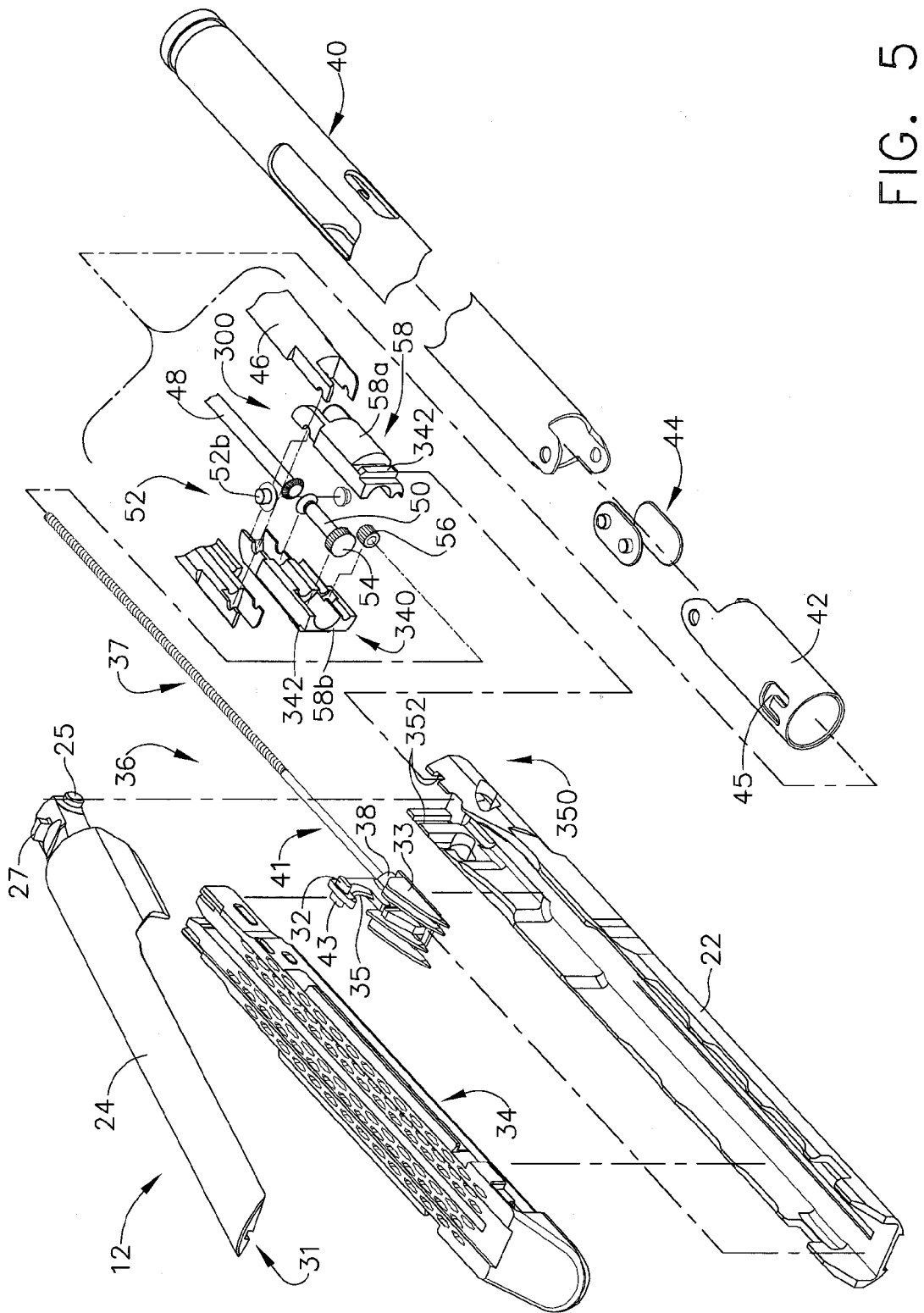
FIG. 5 is an exploded assembly view of an end effector and shaft of the instrument according to various embodiments of the present invention.

FIG. 5 is an exploded view of the end effector 12 according to various embodiments. As shown in the illustrated embodiment, the end effector 12 may include, in addition to the previously-mentioned channel 22 and anvil 24, a knife supporting assembly 32, a sled 33, a staple cartridge 34 that is removably seated in the channel 22, and a flexible drive shaft 36. As used herein, the term "flexible" means easily capable of non-permanently flexing greater than 30 degrees with little resisting to flexing when a flexure force or motion is applied thereto and also capable of returning to a non-flexed state upon removal of the flexure force or motion therefrom. The drive shaft 36 may have a proximal portion with a helical thread 37 formed thereon and a distal portion that is non-threaded. The knife supporting assembly 32 may support a knife 35 in a known manner.

The anvil 24 may have trunnions 25 thereon that enable the anvil 24 to pivot between open and closed positions relative to the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot on the trunnions 25 into the clamped or closed position. If clamping of the end effector 12 is satisfactory, the operator may actuate the firing trigger 20, which, as explained in more detail below, causes the knife supporting assembly 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue.

As can be further seen in FIG. 5, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a secondary drive gear 54 that engages a tertiary drive gear 56 of the flexible drive shaft 36.

Figure 6:
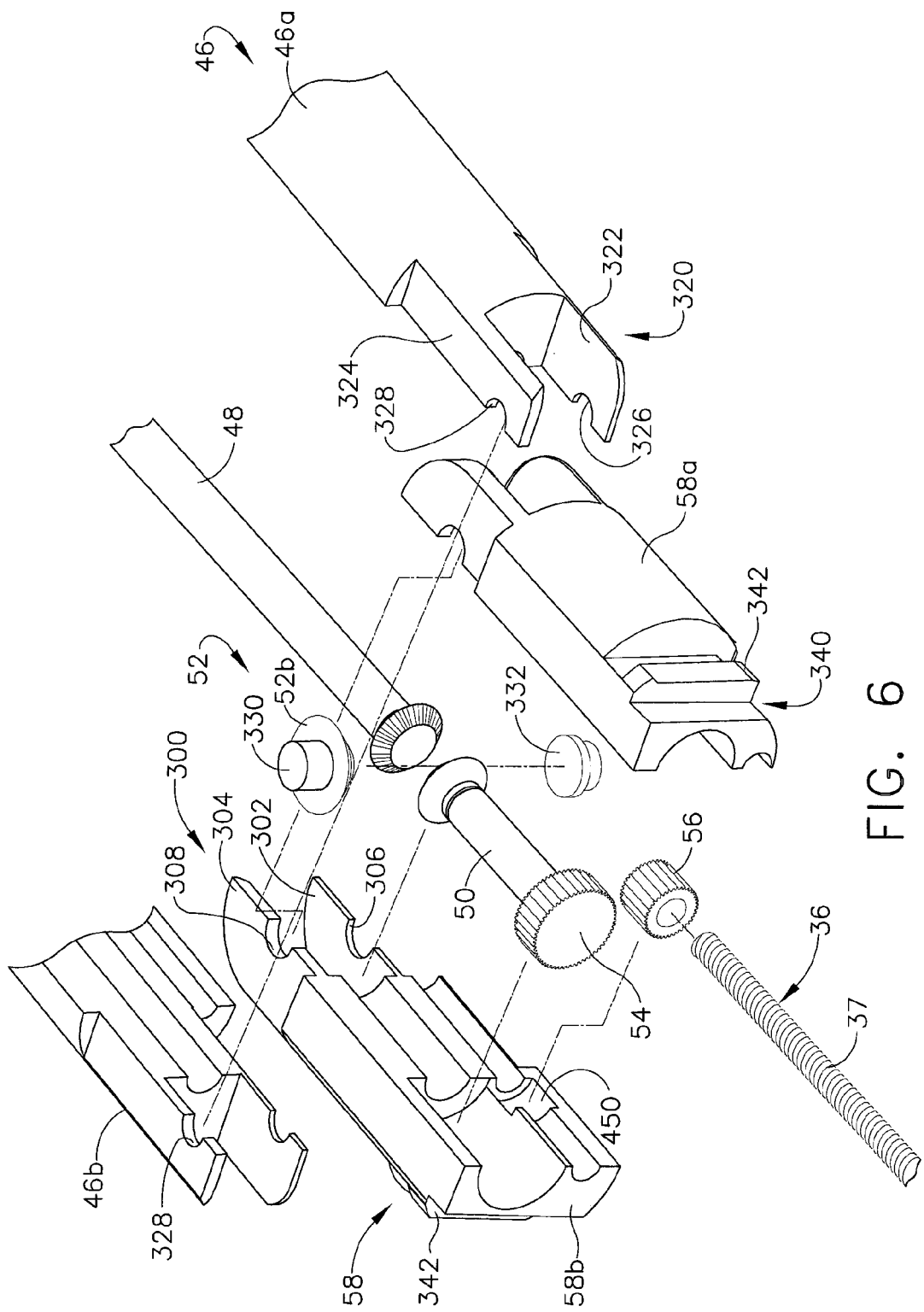
FIG. 6 is an exploded assembly view of a bevel gear assembly and drive shaft arrangement according to various embodiments of the present invention.
Figure 9:
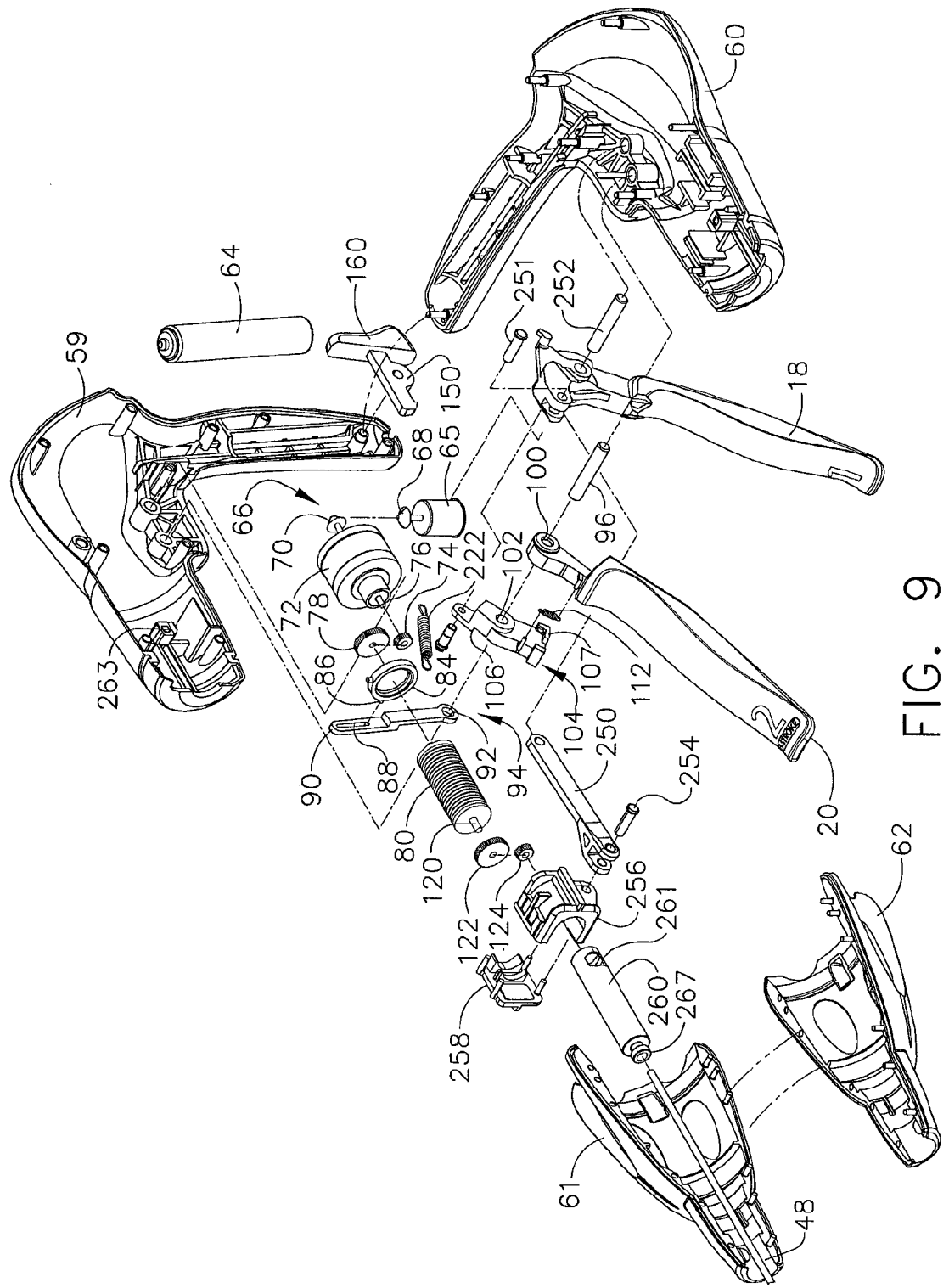
FIG. 9 is an exploded assembly view of a handle according to various embodiments of the present invention.

A distal spine tube 58 assembly may be used to enclose the secondary drive shaft 50 and the drive gears 54, 56. The distal spine tube assembly 58 may be fabricated in two segments 58a and 58b for assembly purposes. The segments 58a and 58b may be retained together by adhesive, snap features, screws, etc. As can be most particularly seen in FIGS. 4 and 6, the proximal end 300 of the distal spine tube assembly 58 has a pair of spaced arms 302, 304 that are configured to support the articulation assembly (e.g., the bevel gear assembly 52a-c) therebetween. Arm 302 has a hole 306 therethrough and arm 304 has a hole 308 therethrough that is coaxially aligned with hole 306. Similarly, the distal end 320 of the proximate spine tube 46 has a lower arm 322 and an upper arm 324 formed thereon. The proximate spine tube 46 may be fabricated in two segments 46a and 46b for assembly purposes. The segments 46a and 46b may be retained together by adhesive, snap features, screws, etc. A hole 326 extends through the lower arm 322 and a hole 328 extends through the arm 324. When assembled together, holes 306, 308, 326, 328 are coaxially aligned to define a pivot axis "PA-PA" that is substantially transverse to the longitudinal axis "L-L". The vertical bevel gear 52b has a shaft portion 330 that is rotatably supported in coaxially aligned holes 308, 328. A coupling axle 332 is similarly rotatably supported in coaxially aligned holes 306, 326. Collectively, the main drive shaft 48, the secondary drive shaft 50, and the articulation assembly (e.g., the bevel gear assembly 52a-c) are sometimes referred to herein as the "main drive shaft assembly". The distal end 340 of the distal spine tube 58 may have a pair of vertically extending columns 342 formed thereon that are configured to extend into slots 352 formed in a proximal end 350 of the elongate channel 22. Such joint arrangement facilitates pivotal travel of the elongate channel 22 about pivot axis "PA-PA" relative to the proximate spine tube 46.

Accordingly, when the main drive shaft 48 is caused to rotate by actuation of the firing trigger 20 (as explained in more detail below), the bevel gear assembly 52a-c causes the secondary drive shaft 50 and drive gear 54 to rotate. The drive gear 56 is rotatably supported within a cavity 450 formed in the distal spine tube assembly 58 and is threadably received on the threaded portion 37 of the flexible drive shaft 36. Collectively, gears 54 and 56 may be referred to herein as a "gear train". Thus, rotation of the drive gear 56 in one direction drives the flexible drive shaft 36 such that the knife supporting assembly 32 and sled 33 are driven in the distal direction "DD" and rotation of the drive gear 56 in an opposite direction causes the drive shaft 36 to rotate in an opposite direction to thereby cause the knife supporting assembly 32 and 33 to be driven in the proximal direction "PD". See FIG. 4.

In various embodiments, the knife supporting assembly 32 and sled 33 are configured to move as a unit. The sled 33 may be made of, for example, plastic, and may have a sloped distal surface. As the sled 33 traverse the channel 22, the sloped forward surface may push up or drive driver members (not shown) in the staple cartridge that each support one or more staples thereon such that as the drivers are driven toward the anvil by the sled 33, the staples supported by the driver members are driven through the clamped tissue and against the anvil 24. The anvil 24 forms the staples, thereby stapling the severed tissue.

In an embodiment wherein the distal end 39 of the flexible drive shaft 36 is rotatably journaled in a bearing 38 in the knife supporting assembly 32 or otherwise rotatably affixed to the knife driving member 32, after the knife driving member has been driven to the desired distal-most position in the channel 22, the drive shaft 36 is rotated in an opposite direction to cause the knife supporting assembly 32 to move in the proximal direction "PD" to a starting position wherein the spent staple cartridge 34 may be removed from the elongate channel 22 and replaced with a new cartridge 34. See FIG. 4. Thus, in those embodiments, the knife supporting assembly 32 and knife 35 supported thereon are reusable for another stapling and cutting procedure.

In other embodiments, the knife supporting assembly 32, knife 35, and sled 33 are provided in the staple cartridge 34. That is, in such embodiments, the knife supporting assembly 32 and the sled 33 are located in the proximal end portion of a fresh (unfired) staple cartridge ready to be driven distally through the cartridge 34 to sever the tissue and fire (drive) the staples into the anvil 24. In these embodiments, the distal end 41 of the drive shaft 36 is not coupled to the knife supporting assembly 32 but instead is configured to bear upon the knife supporting assembly 32 to push it distally through the cartridge 34. Once the knife supporting assembly 32 has been driven to the desired distal-most position in the staple cartridge 34 and the cutting and stapling operations are complete, the user simply reverses the rotation of the drive shaft 48 which drives the drive shaft 36 in the proximal direction back into the closure tube 40 to a starting position. The knife supporting assembly 32 remains in the distal-most position to be discarded with the cartridge 34.

In various embodiments, the knife supporting assembly 32 may be formed with laterally extending tabs 43 formed on the vertically extending knife portion 35. See FIGS. 7 and 8. The vertically extending knife portion 35 may be configured to extend into a longitudinally extending slot 31 formed in the anvil 24. The laterally extending tabs 43 are also received in corresponding slots (not shown) formed in the anvil 24 such that as the knife supporting assembly 32 is driven through the cartridge 34, the knife supporting assembly 32 (by means of the tabs 43) serves to retain the anvil 24 in its clamping position. However, once the knife supporting assembly 32 has been driven to its distal-most position, the tabs 43 are able to disengage those slots through strategically located openings (not shown) in the anvil 24 to permit the anvil 24 to be moved to the open position by the closure tube. Thus, such arrangement enables a fresh knife to be used in connection with each use of the instrument.

In other embodiments, however, the distal end 41 of the drive shaft 36 may be received in a bearing 38 mounted in the knife supporting assembly 32 to facilitate rotation of drive shaft 36 relative thereto yet affix the distal end 41 of the drive shaft 36. Such arrangement enables the drive shaft 36 to rotate relative to the knife supporting assembly 32 while pushing it in the distal direction upon receipt of a rotary motion in a first direction and to pull the knife supporting assembly 32 back to a starting position when another rotary motion is applied thereto in a second opposite direction. Such arrangement pulls the knife supporting assembly 32 in the proximal direction "PD" to a starting position wherein the spent staple cartridge 34 can be removed from the channel 22 and replaced with a fresh cartridge. See FIG. 4. Thus, in these embodiments, the knife 35 is reusable and remains with the instrument 10. In other embodiments, the knife and knife supporting assembly may stay with the cartridge after firing.

Those of ordinary skill in the art will appreciate that the unique and novel features of the drive shaft embodiments described above provide several advantages over prior arrangements. The various embodiments of the present invention may be effectively employed with articulatable end effectors. Some embodiments may be used with cartridges that each have a fresh cutting knife provided therein. Whereas other embodiments are configured to enable the cutting knife arrangement to be reused.

The various embodiments may be driven by a variety of different rotary drive configurations that are known in the art. For example, the drive shaft 48 may be manually rotated or be rotated by means of a motor arrangement supported in the handle of the instrument. The motor may be pneumatically or electrically powered. Thus, the scope of protection afforded to the various drive shaft embodiments of the present invention should not be limited to a particular type of driver (i.e., a motor or manually powered system). One drive system arrangement is disclosed in U.S. Patent Application Publication No. US 2007/0175959 A1 which has been herein incorporated by reference in its entirety.

FIGS. 7-10 illustrate an exemplary embodiment of a motor-driven endocutter, and in particular the handle thereof, that provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. The battery 64 powers a motor 65 disposed in an upper portion of the pistol grip portion 26 of the handle 6. According to various embodiments, the motor 65 may be a DC brushed driving motor having a maximum rotation of, approximately, 5000 RPM. The motor 65 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

Figure 12:
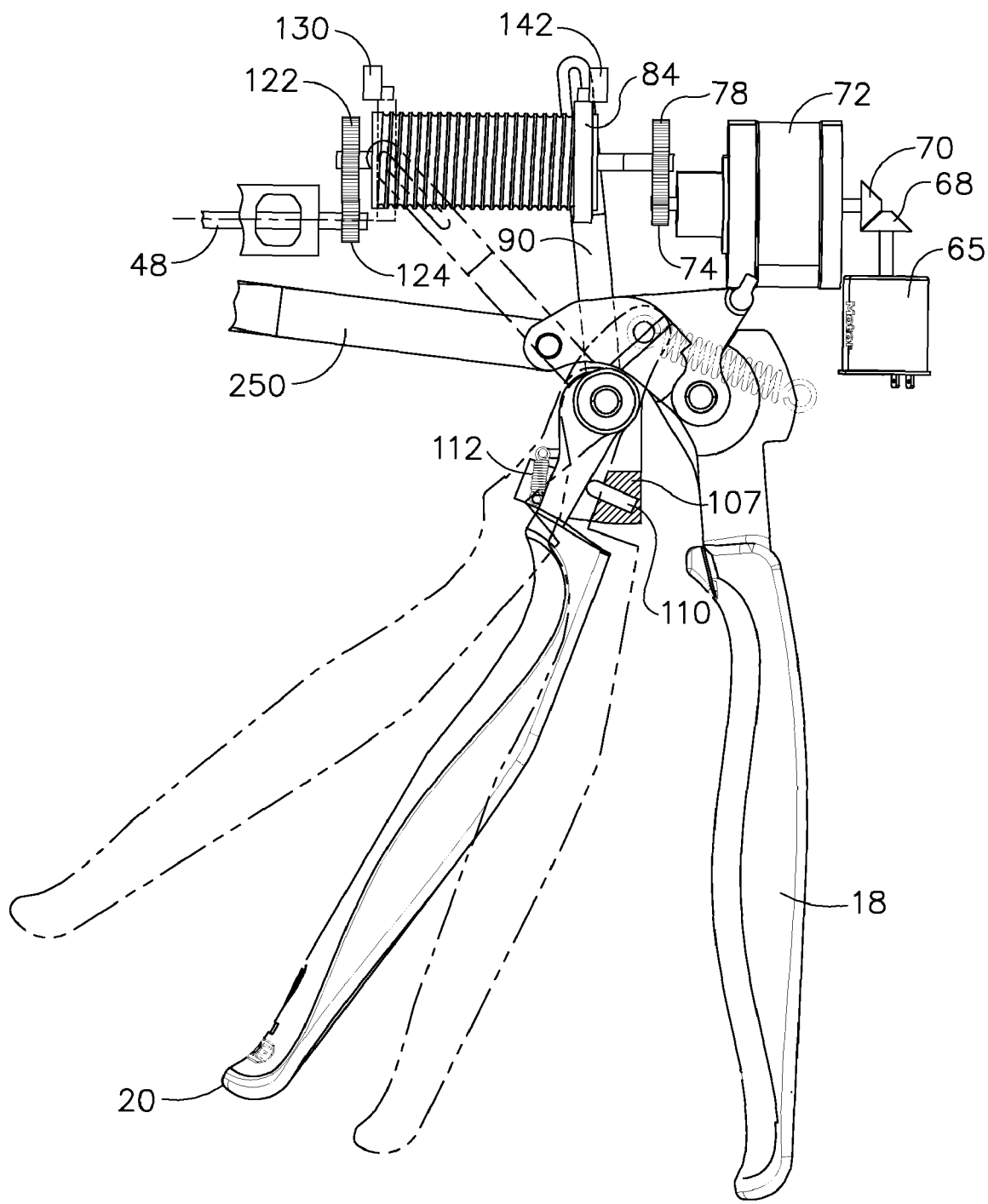
FIG. 12 is a side view of the closure and firing trigger arrangements of FIG. 11.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. See FIG. 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 110, to thereby stop the motor 65. As such, the user may stop the deployment of the end effector 12, thereby providing a measure of control of the cutting/fastening operation to the operator.

The distal end of the helical gear drum 80 may include a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife supporting assembly 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife supporting assembly 32 in the end effector 12. That is, the knife supporting assembly 32 and sled 33 are caused to traverse the channel 22 longitudinally, thereby cutting tissue clamped in the end effector 12.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the drive shaft 36 to retract, and also causes the ring 84 on the helical gear drum 80 to move back to the proximate end of the helical gear drum 80.

Figure 10:
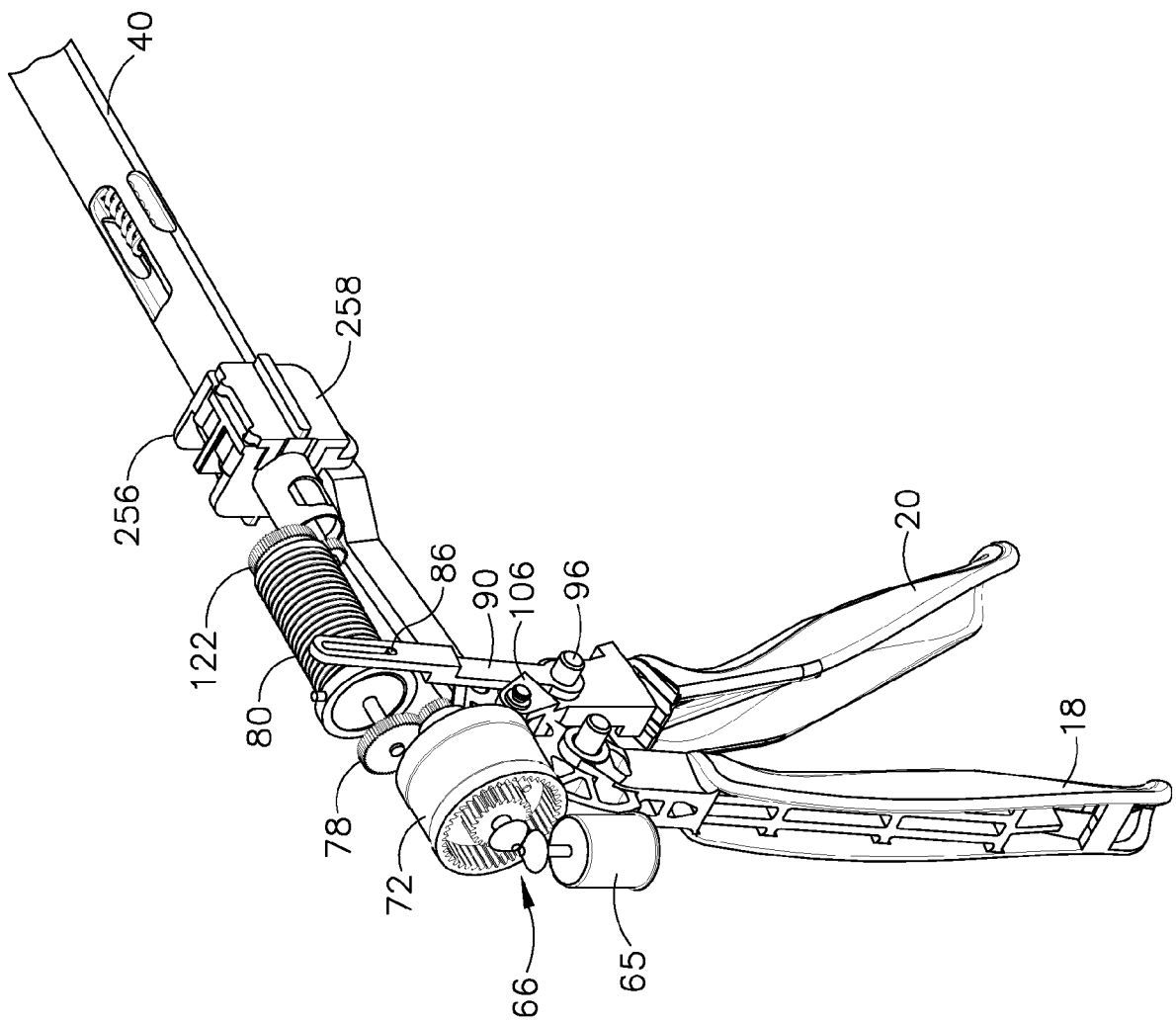
FIG. 10 is another perspective view of portions of the closure trigger and firing trigger arrangements according to various embodiments of the present invention.
Figure 11:
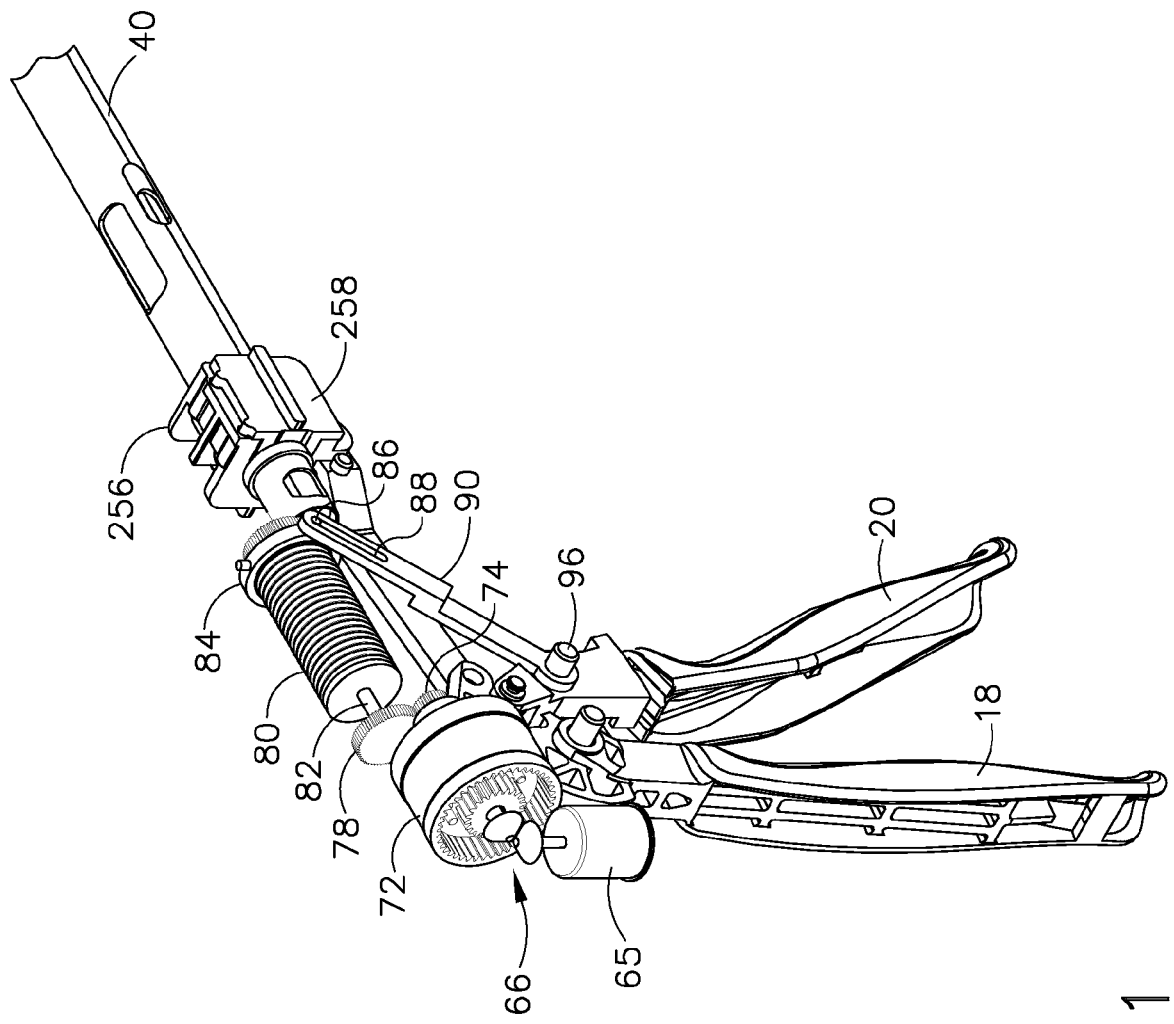
FIG. 11 is another perspective view of the closure and firing trigger arrangements depicted in FIG. 10.

The middle handle piece 104 includes a backside shoulder 106 that engages the slotted arm 90 as best shown in FIGS. 10 and 11. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Components of an exemplary closure system for closing (or clamping) the anvil 24 of the end effector 12 by retracting the closure trigger 18 are also shown in FIGS. 9-12. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. A spring 222 may be affixed to the closure trigger 18 and one of the handle side pieces 59, 60 to bias the closure trigger 18 to an open position in a known manner. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that is configured to be coupled to the proximate spine tube 46.

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate into the clamped or closed position. A slide button 160 and a hook 150 may be employed to releasably lock the closure trigger 18 in a "closed" or locked position as described in further detail in U.S. Patent Application Publication No. US 2007/0175959A1 which has been herein previously incorporated by reference. See FIG. 9. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 13:
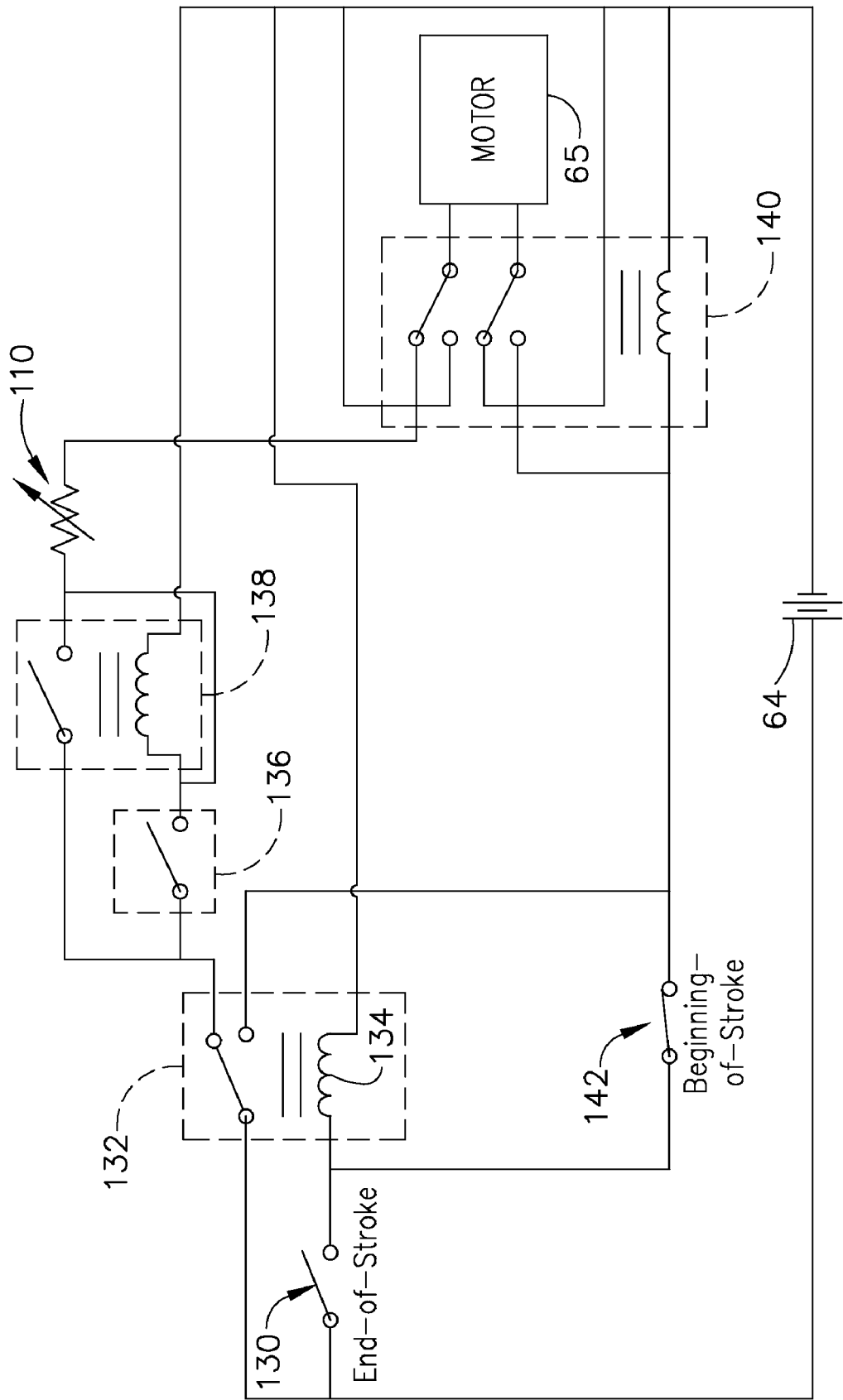
FIG. 13 is a schematic diagram of a circuit that may be used in the instrument according to various embodiments of the present invention.

FIG. 13 is a schematic diagram of an electrical circuit of the instrument 10 according to various embodiments of the present invention. When an operator initially pulls in the firing trigger 20 after locking the closure trigger 18, the sensor 110 is activated, allowing current to flow there through. If the normally-open reverse motor sensor switch 130 is open (meaning the end of the end effector stroke has not been reached), current will flow to a single pole, double throw relay 132. Since the reverse motor sensor switch 130 is not closed, the inductor 134 of the relay 132 will not be energized, so the relay 132 will be in its non-energized state. The circuit also includes a cartridge lockout sensor 136. If the end effector 12 includes a staple cartridge 34, the sensor 136 will be in the closed state, allowing current to flow. Otherwise, if the end effector 12 does not include a staple cartridge 34, the sensor 136 will be open, thereby preventing the battery 64 from powering the motor 65.

When the staple cartridge 34 is present, the sensor 136 is closed, which energizes a single pole, single throw relay 138. When the relay 138 is energized, current flows through the relay 136, through the variable resistor sensor 110, and to the motor 65 via a double pole, double throw relay 140, thereby powering the motor 65 and allowing it to rotate in the forward direction.

When the end effector 12 reaches the end of its stroke, the reverse motor sensor 130 will be activated, thereby closing the switch 130 and energizing the relay 134. This causes the relay 134 to assume its energized state, which causes current to bypass the cartridge lockout sensor 136 and variable resistor 110, and instead causes current to flow to both the normally-closed double pole, double throw relay 142 and back to the motor 65, but in a manner, via the relay 140, that causes the motor 65 to reverse its rotational direction.

Because the stop motor sensor switch 142 is normally-closed, current will flow back to the relay 134 to keep it closed until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Although the present invention has been described herein in connection with certain disclosed embodiments, many modifications and variations to those embodiments may be implemented. For example, different types of end effectors may be employed. In addition, various embodiments may comprise obtaining a surgical cutting and fastening instrument as described above, sterilizing the surgical cutting and fastening instrument and storing the surgical cutting and fastening instrument in a sterile container. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical cutting and fastening instrument comprising:
a handle assembly;
a generator of rotary motion supported by said handle assembly;
an elongate shaft assembly operably coupled to said handle assembly and defining an elongate axis;
an elongate channel coupled to said elongate shaft for selective pivotal travel about a pivot axis that is substantially transverse to said elongate axis, said elongate channel sized to operably support a staple cartridge therein; and
a rotary drive system comprising:
a main drive shaft assembly operably interfacing with said generator of rotary motion;
a gear train in meshing engagement with said main drive shaft for receiving said rotary motion therefrom; and
a flexible drive shaft in meshing engagement with said gear train, said flexible drive shaft further having a distal end non-threadably coupled to a knife supporting assembly in said elongate channel such that said flexible drive shaft can rotate relative thereto to drive said knife supporting assembly in a distal direction upon receipt of a rotary motion in a first direction from said gear drive train and wherein upon receipt of another rotary motion in a second direction from said gear drive train, said flexible drive shaft pulls said knife supporting assembly in a proximal direction.

2. The surgical cutting and fastening instrument of claim 1, wherein said distal end of said flexible drive shaft is coupled to said knife supporting assembly by a bearing.

3. The surgical cutting and fastening instrument of claim 1, wherein said gear train comprises:
a first gear coupled to said main drive shaft;
a second gear in meshing engagement with said first gear; and
a third gear coupled to a secondary drive shaft and in meshing engagement with said second gear.

4. The surgical cutting and fastening instrument of claim 3, wherein said secondary drive shaft has a secondary drive gear thereon in meshing engagement with a tertiary gear in meshing engagement with said flexible drive shaft.

5. The surgical cutting and fastening instrument of claim 4, wherein said tertiary gear is in meshing engagement with said flexible drive shaft and is rotatably retained within a distal spine tube assembly supported within said elongate shaft assembly.

6. The surgical cutting and fastening instrument of claim 5, wherein said second gear rotates about said pivot axis.

7. A method for processing a device for surgery, the method comprising:
obtaining the surgical cutting and fastening instrument of claim 1;
sterilizing the surgical cutting and fastening instrument; and
storing the surgical cutting and fastening instrument in a sterile container.

8. A surgical cutting and fastening instrument comprising:
a handle assembly;
a generator of rotary motion supported by said handle assembly;
an elongate shaft assembly operably coupled to said handle assembly and defining an elongate axis;
an elongate channel coupled to said elongate shaft for selective pivotal travel about a pivot axis that is substantially transverse to said elongate axis, said elongate channel sized to removably support a disposable staple cartridge therein that has a knife supporting assembly therein;
a rotary drive system comprising:
a main drive shaft assembly operably interfacing with said generator of rotary motion;
a gear train in meshing engagement with said main drive shaft for receiving said rotary motion therefrom; and
a flexible drive shaft movably supported in said elongate shaft and in meshing engagement with said gear train and oriented to extend axially into said disposable staple cartridge, said flexible drive shaft having a distal end oriented to impart an axial pushing motion to said knife supporting assembly without being attached to said knife supporting assembly to drive said knife supporting assembly in a distal direction within said disposable staple cartridge upon receipt of a rotary motion in a first direction from said gear drive train and to return into said elongate shaft upon receipt of a rotary motion in a second direction from said gear drive train.

9. The surgical cutting and fastening instrument of claim 8 wherein said gear train comprises:
a first gear coupled to said main drive shaft;
a second gear in meshing engagement with said first gear; and
a third gear coupled to a secondary drive shaft and in meshing engagement with said second gear.

10. The surgical cutting and fastening instrument of claim 9, wherein said secondary drive shaft has a secondary drive gear thereon in meshing engagement with a tertiary gear in meshing engagement with said flexible drive shaft.

11. The surgical cutting and fastening instrument of claim 10 wherein said tertiary gear is in meshing engagement with said flexible drive shaft and is rotatably retained within a distal spine tube assembly supported within said elongate shaft assembly.

12. A surgical cutting and fastening instrument comprising:
a handle assembly;
a generator of rotary motion supported by said handle assembly;

an elongate shaft assembly operably coupled to said handle assembly and defining an elongate axis;

an elongate channel coupled to said elongate shaft for selective pivotal travel about a pivot axis that is substantially transverse to said elongate axis, said elongate channel sized to removably support a staple cartridge therein;

a reusable knife supporting assembly operably supported within said elongate channel for selective axial travel therein from a starting position to an ending position and back to said starting position; and a rotary drive system comprising:
   a main drive shaft assembly operably interfacing with said generator of rotary motion;
   a gear train in meshing engagement with said main drive shaft for receiving said rotary motion therefrom; and
   a flexible drive shaft having a distal end nonthreadably coupled to said reusable knife supporting assembly and movably supported in said elongate shaft such that said flexible drive shaft may be selectively rotated relative to said reusable knife supporting assembly, said flexible drive shaft in meshing engagement with said gear train and oriented to extend axially into said staple cartridge to drive said knife supporting assembly from said starting position to said ending position upon receipt of a rotary motion in a first direction from said gear drive train and to return said knife supporting assembly to said starting position upon receipt of a rotary motion in a second direction from said gear drive train.

13. The surgical cutting and fastening instrument of claim 12 wherein said gear train comprises:
a first gear coupled to said main drive shaft;
a second gear in meshing engagement with said first gear; and
a third gear coupled to a secondary drive shaft and in meshing engagement with said second gear.

14. The surgical cutting and fastening instrument of claim 13 wherein said secondary drive shaft has a secondary drive gear thereon in meshing engagement with a tertiary gear in meshing engagement with said flexible drive shaft.

15. The surgical cutting and fastening instrument of claim 14 wherein said tertiary gear is in meshing engagement with said flexible drive shaft and is rotatably retained within a distal spine tube assembly supported within said elongate shaft assembly.

16. The surgical cutting and fastening instrument of claim 13, wherein said second gear rotates about said pivot axis.

17. The surgical cutting and fastening instrument of claim 8 wherein, upon application of said rotary motion in said first direction to said flexible drive shaft, said flexible drive shaft moves axially in a distal direction.

18. A surgical cutting and fastening instrument comprising:
a handle assembly;
a generator of rotary motion supported by said handle assembly;
an elongate shaft assembly operably coupled to said handle assembly and defining an elongate axis;
an elongate channel coupled to said elongate shaft for selective pivotal travel about a pivot axis that is substantially transverse to said elongate axis, said elongate channel sized to operably support a staple cartridge therein; and
a rotary drive system comprising:
   a main drive shaft assembly operably interfacing with said generator of rotary motion;
   a gear train in meshing engagement with said main drive shaft for receiving said rotary motion therefrom; and
   a flexible drive shaft in meshing engagement with said gear train, said flexible drive shaft further having a distal end configured to apply an axial pushing motion to a knife supporting assembly in said elongate channel without being coupled thereto to drive said knife supporting assembly in a distal direction upon receipt of a rotary motion in a first direction from said gear drive train.

19. The surgical cutting and fastening instrument of claim 18 wherein, upon application of said rotary motion in said first direction to said flexible drive shaft, said flexible drive shaft moves axially in a distal direction.

20. The surgical cutting and fastening instrument of claim 19 wherein upon application of another rotary motion in a second direction to said flexible drive shaft, said flexible drive shaft moves axially in a proximal direction.

* * * * *